US006971384B2

(12) United States Patent
Gieschen et al.

(10) Patent No.: US 6,971,384 B2
(45) Date of Patent: Dec. 6, 2005

(54) DRY POWDER INHALER

(75) Inventors: Andrew W. Gieschen, San Diego, CA (US); Michael Ligotke, San Diego, CA (US); Jeffrey Chen, San Diego, CA (US); Charles Ganem, San Diego, CA (US); Bernard Greenspan, San Diego, CA (US)

(73) Assignee: Quadrant Technologies Limited, Nottingham (GB)

( * ) Notice: Subject to any disclaimer, the term of this patent is extended or adjusted under 35 U.S.C. 154(b) by 0 days.

(21) Appl. No.: 10/782,449

(22) Filed: Feb. 19, 2004

(65) Prior Publication Data

US 2004/0163644 A1    Aug. 26, 2004

Related U.S. Application Data

(63) Continuation of application No. 09/773,261, filed on Jan. 31, 2001, now Pat. No. 6,715,486, which is a continuation-in-part of application No. 09/495,494, filed on Feb. 1, 2000, now Pat. No. 6,427,688.

(51) Int. Cl.⁷ ............................................. A61M 15/00
(52) U.S. Cl. ........................... 128/203.15; 128/203.12; 604/58
(58) Field of Search .................... 128/203.15, 203.23, 128/203.12, 200.22; 604/58

(56) References Cited

U.S. PATENT DOCUMENTS

| | | |
|---|---|---|
| 2,470,296 A | 5/1949 | Fields |
| 2,470,297 A | 5/1949 | Fields |
| 2,534,636 A | 12/1950 | Stirn |
| 2,816,549 A | 12/1957 | Webster |
| 3,362,405 A | 1/1968 | Hazel |
| 3,809,084 A | 5/1974 | Hansen |
| 3,861,210 A | 1/1975 | Giverus |
| 4,452,239 A | 6/1984 | Malem |
| 4,509,515 A | 4/1985 | Altounyan et al. |
| 4,790,305 A | 12/1988 | Zoltan et al. |
| 4,841,964 A | 6/1989 | Hurka et al. |
| 4,860,740 A | 8/1989 | Kirk et al. |
| 5,042,472 A | 8/1991 | Bunin |
| 5,048,514 A | 9/1991 | Ramella |
| 5,492,112 A | 2/1996 | Mecikalski et al. |
| 5,522,383 A | 6/1996 | Calvert et al. |
| 5,596,982 A | 1/1997 | Blaha-Schnabel |
| 5,619,984 A | 4/1997 | Hodson et al. |
| 5,642,727 A | 7/1997 | Datta et al. |
| 5,714,007 A | 2/1998 | Pletcher et al. |
| 5,797,391 A | 8/1998 | Cook et al. |
| 6,007,630 A | 12/1999 | Pletcher et al. |

(Continued)

FOREIGN PATENT DOCUMENTS

EP    0407028 A2    5/1990

(Continued)

*Primary Examiner*—Mital Patel
(74) *Attorney, Agent, or Firm*—Perkins Coie LLP

(57) ABSTRACT

A dry powder inhaler has a dispersion chamber containing beads. A dose of dry powder is released into the chamber, or into an inlet tangentially joining into the chamber. As the patient inhales on a nosepiece or mouthpiece, air moves circularly through the dispersion chamber to drive the beads. The beads roll, bounce, and collide repeatedly with the drug particles on the chamber surfaces or on the beads. The smaller active drug particles are separated from larger carrier particles and from each other, and a powder aerosol is created and inhaled by the patient. The beads are preferably lightweight, so that they can be rapidly accelerated and moved, even with nominal inspiration. The flow resistance of the inhaler is also reduced via the beads, allowing greater airflow and powder dispersion, without any increased effort by the patient.

19 Claims, 13 Drawing Sheets

U.S. PATENT DOCUMENTS

| | | |
|---|---|---|
| 6,063,194 A | 5/2000 | Poliniak et al. |
| 6,073,629 A | 6/2000 | Hardy et al. |
| 6,074,688 A | 6/2000 | Pletcher et al. |
| 6,089,227 A | 7/2000 | Nilsson |
| 6,096,368 A | 8/2000 | Sun |
| 6,125,998 A | 10/2000 | Batista |
| 6,230,707 B1 | 5/2001 | Horlin |
| 6,418,926 B1 | 7/2002 | Chawla |
| 6,427,688 B1 * | 8/2002 | Ligotke et al. ........ 128/203.15 |
| 6,715,486 B2 * | 4/2004 | Gieschen et al. ...... 128/203.15 |

FOREIGN PATENT DOCUMENTS

| | | |
|---|---|---|
| EP | 0407028 A3 | 5/1990 |
| EP | 0504459 A1 | 9/1992 |
| FR | 2352556 | 12/1977 |
| GB | 654860 | 7/1951 |
| GB | 2179260 A | 3/1987 |
| SE | 7509342-7 | 7/1983 |
| WO | WO 90/15635 | 12/1990 |
| WO | WO 95/03846 | 2/1995 |

* cited by examiner

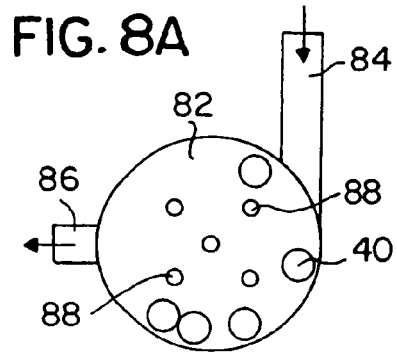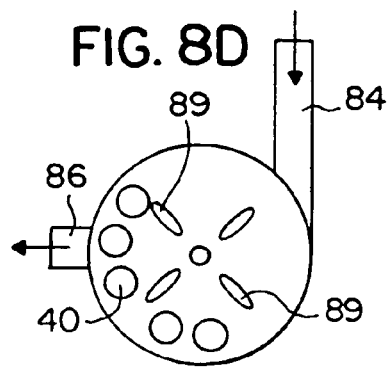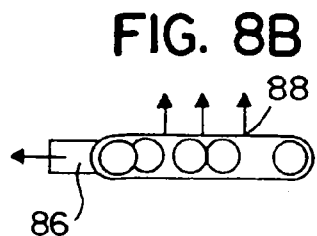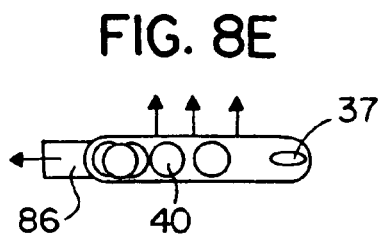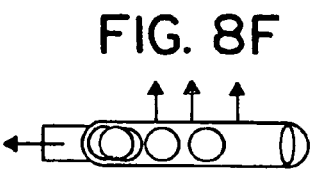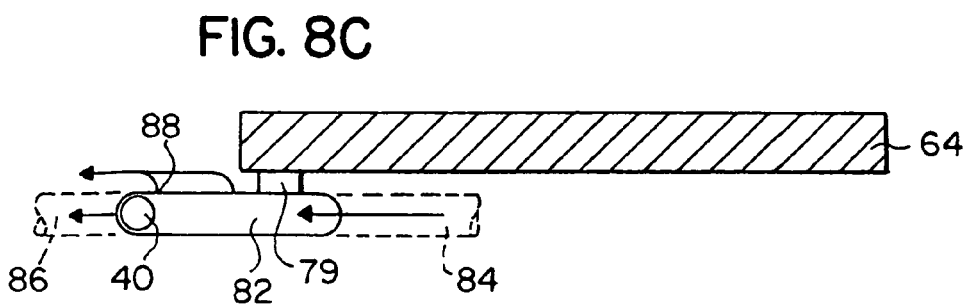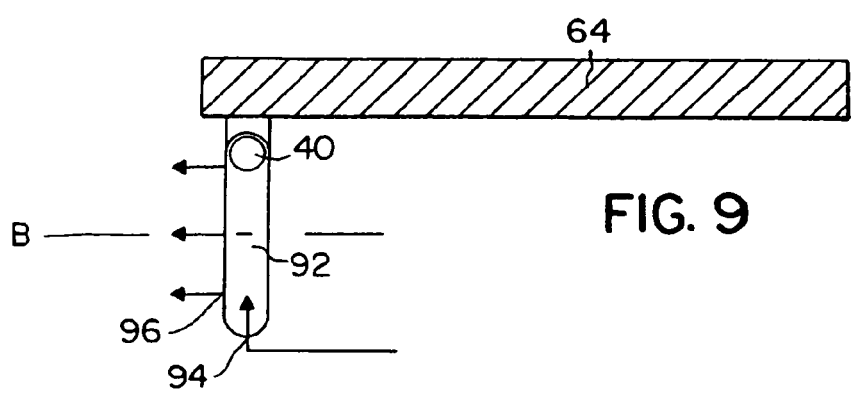

TABLE WITH RESISTANCE DATA (MS EXCEL PICTURE):

TABLE: NUMBER OF BEADS VERSUS INHALER RESISTANCE TO AIR FLOW

| NUMBER OF BEADS | AIR FLOW RESISTANCE (cmH2O^0.5/Lpm) | |
| --- | --- | --- |
| | ONE-JET INHALER | TWO-JET INHALER |
| 0 | 1.08 | |
| 1 | 0.92 | 0.73 |
| 2 | 0.83 | |
| 3 | 0.79 | 0.53 |
| 4 | 0.76 | |
| 5 | 0.75 | |
| 6 | 0.74 | 0.44 |
| 10 | 0.72 | |
| 11 | 0.72 | |
| *12 | 0.67 TO 1.7 | |

*RESISTANCE MEASUREMENTS FLUCTUATE WHEN 12 OR MORE BEADS ARE USED; THIS IS SHOWN BY THE DASHED LINE IN THE FIGURE

FIG. 17

AEROSOL PERFORMANCE DATA WITH DRY POWDER FORMULATION OF BUDESONIDE AND LACTOSE

| INHALER MODEL | MODEL 1 | MODEL 2 | MODEL 3 |
|---|---|---|---|
| TESTED WITH MOUTHPIECE | NO | YES | YES |
| NUMBER OF AIR JETS IN MODEL | 2 | 1 | 2 |
| TOTAL AIR FLOW, Lpm | 15 | 15 | 28 |
| BEAD CHAMBER AIR FLOW (APPROX.), Lpm | 15 | 9 | 16 |
| AIR-FLOW PRESSURE DROP, cmH20 | 44 | 24 | 51 |
| RESISTANCE, cmH20^0.5/Lpm | 0.44 | 0.33 | 0.25 |
| RESPIRABLE FRACTION, FIRST SAMPLE, % | 36.2 | 43.1 | 43.6 |
| RESPIRABLE FRACTION, SECOND SAMPLE, % | 34.0 | 43.2 | 43.3 |
| RESPIRABLE FRACTION, THIRD SAMPLE, % | 37.5 | 43.9 | 43.9 |
| RESPIRABLE FRACTION, FOURTH SAMPLE, % | 37.5 | 41.2 | 47.8 |
| RESPIRABLE FRACTION (AVERAGE), % | 36.3 | 42.9 | 44.7 |
| RESPIRABLE FRACTION, STANDARD DEVIATION, % | 1.7 | 1.2 | 2.1 |

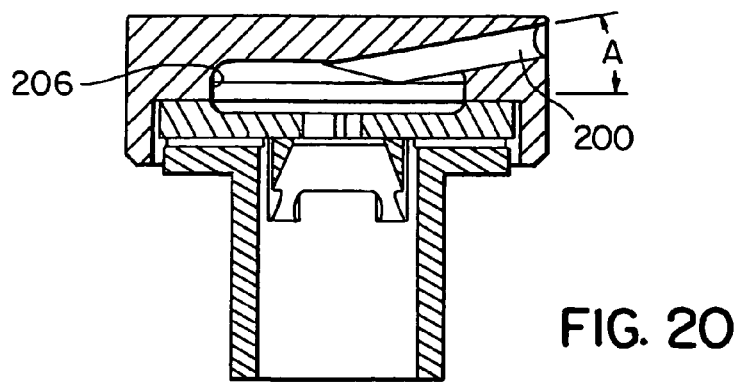
FIG. 20
FIG. 21
SCOOP JET
FIG. 22
CHORDED JET
FIG. 23
TANGENT JET
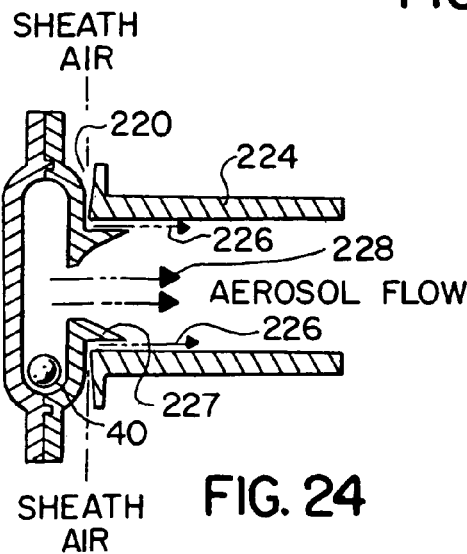
FIG. 24
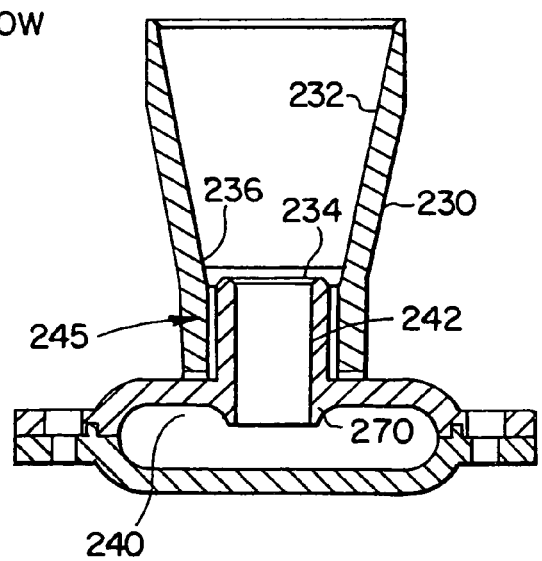
FIG. 25

3 OUTLET
HOLES

SINGLE
OUTLET HOLE

SLOTTED
OUTLET HOLE

DRY POWDER INHALER

This application is a Continuation of U.S. patent application Ser. No. 09/773,261, filed Jan. 31, 2001, now U.S. Pat. No. 6,715,486, which is a Continuation-in-Part of U.S. patent application Ser. No. 09/495,494, filed Feb. 1, 2000, now U.S. Pat. No. 6,427,688, all of which are incorporated herein by reference.

The field of the invention is inhalers.

BACKGROUND OF THE INVENTION

Inhalers are used to deliver drugs into a patient's lungs. Typically, an inhaler contains or provides a mixture of drug particles and air or propellant gas. The mixture is delivered via the patient inhaling from a mouthpiece on the inhaler with the air or propellant gas carrying the drug particles into the patient's lungs.

In dry powder inhalers, the drug particles, in the form of a fine dry powder, are entrained into an airflow, and inhaled by the patient, for treatment for various conditions, for example, bronchial asthma. Drugs delivered via a dry powder inhaler can be used to treat many conditions, including those unrelated to lung conditions, via the systemic absorption of the drug into the bloodstream, via the lung.

For effective dose delivery using a dry powder inhaler, the powder particles must first be dispersed to form a powder/air aerosol. Various techniques for forming powder aerosols have been proposed. Some of these techniques use the airflow from the patient's inspiration alone to disperse the powder. Other techniques involve forming a powder aerosol by spinning a propeller within a chamber; generating a fast moving flow of air over or through the powder; and shaking, vibrating, or impacting a powder laden string, tape, or mesh, using mechanical devices or ultrasonics. In addition, various other techniques for generating powder aerosols have been proposed or used, with varying degrees of success. Challenges remain in achieving a dry powder inhaler which can effectively create a dry powder aerosol for inhalation, while also having advantages in other areas, such as effectiveness in creating an aerosol, reliability, complexity of design, costs, ergonomics, dose consistency, etc.

Accordingly, it is an object of the invention to provide an improved dry powder inhaler.

SUMMARY OF THE INVENTION

To these ends, in a first aspect, a dry powder inhaler has a dispersion chamber including a bead race. A nosepiece or mouthpiece has at least one outlet opening connecting or entering into the dispersion chamber. One or more inlets also connect into the dispersion chamber. The dispersion chamber contains one or more beads which can move about in the bead race. A powder formulation containing smaller active pharmaceutical particles, and optionally also containing larger inert carrier particles, is placed into or adjacent to the chamber.

When a patient inhales on the mouthpiece, air and powder are drawn into, or flow about within, the dispersion chamber. The beads collide with the interior chamber surfaces, and/or each other, and the powder particles on the chamber surfaces or on the beads. The movement of the beads separate the smaller active drug particles from each other and/or the larger inert carrier particles, if any. In addition to these mechanical forces, other causes of dispersion may include fluid shear between the beads, the powder particles, and the chamber walls. Larger carrier particles, if included in the powder formulation, can further enhance dispersion via enhanced impact energy and abrasion. The active particles are entrained into the airflow through the dispersion chamber, for inhalation by the patient. The larger inert or excipient carrier particles may or may not be entrained and inhaled. The carrier particles are advantageously provided to scour the powder path clean of the fine active particles, so that a more uniform dose may be delivered.

In a separate aspect of the invention, the beads within the dispersion chamber are induced to move chaotically, so that most or all of the interior surfaces of the dispersion chamber, and the surfaces of the beads are contacted. As a result, less of the powder may be held up within the dispersion chamber, and a more uniform dose may be delivered. Flow rate performance may also be improved.

In another separate aspect of the invention, the flow resistance of a dry powder inhaler is reduced by providing one or more beads into the airflow path of the inhaler. As a result, improved dispersion of powder is achieved, with no additional inspiratory effort by the patient.

A dispersion chamber is a chamber or confined area wherein dry powder is dispersed and/or mixed with air. The dispersion chamber may be the only location where powder is dispersed, or it may be one of two or more such locations or powder dispersing or deagglomerizing features. A bead is a loose component not physically attached to any other component or surface of the inhaler, so that it is free to move within the inhaler, with at least one degree of freedom. A bead race is a surface, which a bead contacts, continuously or intermittently. A bead race may be a well-defined or consistent path in or on which beads uniformly move about, or it may be a surface not part of such a path.

The invention resides as well in subcombinations of the components, features, and steps described. While the drawings and written description may disclose features and components in connection with a specific embodiment, the features and components described below may be used, alone or in combinations, with any embodiment.

BRIEF DESCRIPTION OF THE DRAWINGS

FIG. 8A is a schematically illustrated top view of a third embodiment;

FIG. 8B is a side view thereof;

FIG. 8C is a side view of the embodiment of FIGS. 8A and 8B, and also schematically showing a dose reservoir or ring;

FIG. 8D is a schematically illustrated top view of the inhaler shown in FIG. 8A, but with elongated or slit outlets;

FIG. 8E is a side view thereof showing a horizontal elongated or slit inlet;

FIG. 8F is an alternative design having a vertical slit inlet;

FIG. 9 is a schematically illustrated side view of another embodiment;

FIG. 17 is a table of airflow resistance data for the inhalers shown in FIGS. 1 and 8A;

FIG. 19 is a table showing aerosol performance of the inhalers shown in FIGS. 1 and 8A.

FIG. 20 is a section view of a dispersion chamber and mouthpiece for use in an inhaler;

FIG. 21 is a schematic view of a scoop inlet;

FIG. 22 is a schematic view of a chorded inlet;

FIG. 23 is a schematic view of a tangent inlet, as shown in FIG. 1;

FIG. 24 is a section view of a mouthpiece with sheath air;

FIG. 25 is a schematic view of an alternative mouthpiece with sheath air;

DETAILED DESCRIPTION OF THE DRAWINGS

Figure 1:
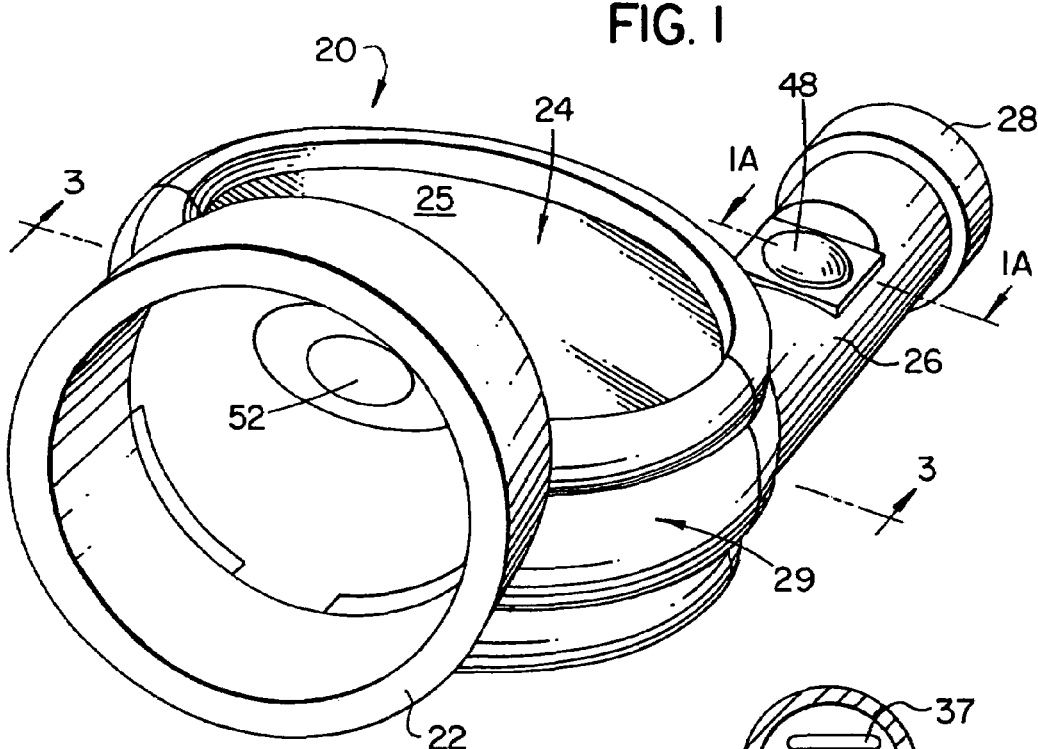
FIG. 1 is a perspective view of a first embodiment of the present inhaler.
Figure 2:
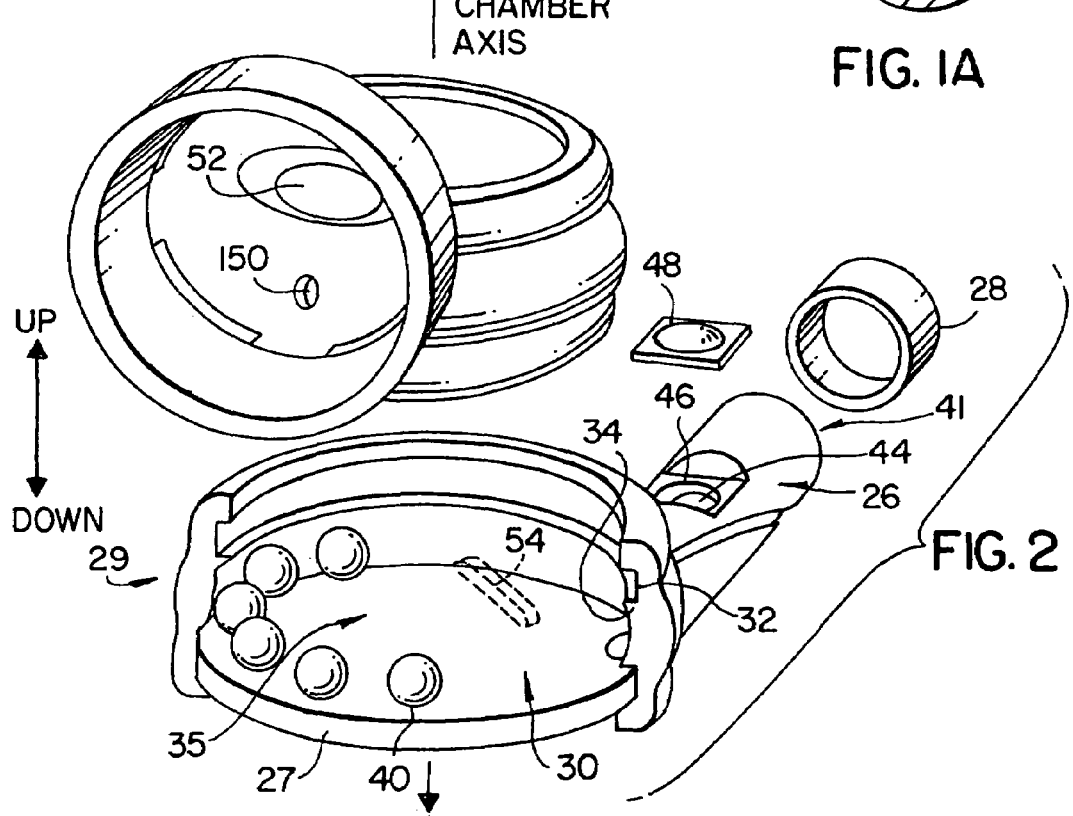
FIG. 2 is an exploded section view thereof.

Turning now in detail to the drawings, as shown in FIGS. 1 and 2, an inhaler 20 has a mouthpiece 22 attached to a housing or body 24. A nosepiece, adapted to engage a patient's nose, may be used in place of the mouthpiece 22, for nasal delivery applications. The term mouthpiece herein means a nose/mouthpiece, i.e., a component adapted to be placed directly or indirectly on, in, over, or against a patients nose or mouth, or both.

The housing includes a top plate 25, a bottom plate 27, and a circumferential wall 29. An inlet 26 is attached to the housing 24. A flow control device 28 is optionally positioned over the inlet 26. The flow control device 28 may be a flow trigger, or a flow controller or limiter, to moderate airflow into the inlet opening 41.

Figure 3:
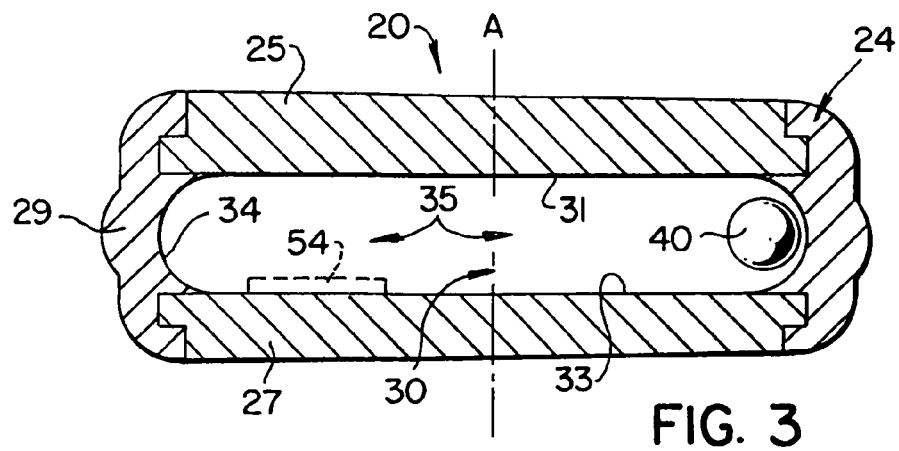
FIG. 3 is a section view taken along line 3—3 of FIG. 1.

Referring to FIGS. 1–3, the circumferential wall 29, upper plate 25 and lower plate 27, which make up the housing 24, enclose or define a dispersion chamber 30. The dispersion chamber 30 has an open central area 35. A race surface 34 is preferably formed on the inside of the circumferential wall 29. The race surface 34 is a round and smoothly curving surface. The race surface is preferably tangent to the inside (lower) surface 31 of the upper plate 25, as well as tangent to the inside (upper) surface 33 of the lower plate 27, so that the surfaces transition smoothly. The inside surfaces 31 and 33 of the upper and lower plates 25 and 27, are preferably flat and smooth. The upper and lower plates are secured into the housing ring 29 via the plate edges inserting into upper and lower annular slots 32, using adhesives, bonding, ultrasonic welding, or other well known attachment techniques. The housing 24 is preferably made of a plastic material. The housing 24, or the entire inhaler 20, may also be integrally molded or manufactured.

Figure 1A:
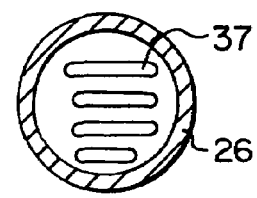
FIG. 1A is a section view taken along line 1A—1A of FIG. 1.

The inlet 26 has an inlet opening or duct 41, preferably joining tangentially into the dispersion chamber 30. The duct 41 may open into the chamber 30 through one or more inlet openings 27, which may be round or elongated slit openings, as shown in FIG. 1A. A dose opening 44 extends through the inlet 26, below a dose platform 46, adapted to receive and hold a dose container 48. Referring still to FIG. 2, one or more outlet openings or a slot 52 connect from the chamber 30 to the interior of the mouthpiece 22. The outlets may be configured in the same way as the inlet openings 37, as described above.

The beads 40 may be multifaceted large drug particles or irregularly shaped crystalline particles, or amorphous drug particles, so that the drug particles themselves can serve as beads. These bead particles may range in size from e.g., 500 microns to 2–4 mm.

One or more beads 40 are contained within the chamber 30. The beads are preferably spherical, but may have other shapes as well, i.e., the beads 40 may be oval or elliptical, disk-shaped, ring-shaped, etc. The race surface preferably has a radius of curvature greater than the radius of curvature of the beads 40 (or of the largest bead 40 if the beads are of different size), so that all of the beads can make contact with all surfaces of the race 34. The dispersion chamber 30 preferably holds from 2–10 beads 40. The beads 40 are preferably made of a lightweight material, such as plastic so that they can be rapidly-accelerated, and easily moved by the air stream flowing through the chamber 30.

The term "characteristic dimension" as used below means the largest dimension (length, width, or height) of the feature or object. Thus, the characteristic dimension of an elliptical bead is the "length" of the bead, i.e., the dimension of the bead taken along its major axis.

The bead 40, or the largest of the beads (i.e., the bead with the largest characteristic dimension) preferably has a characteristic dimension of from 50–90% of the height or thickness of the dispersion chamber, i.e., the dimension between the surfaces 31 and 33. This allows for some vertical bead movement on the race 34, and between the surfaces 31 and 33. The beads can be mixed, with the beads having different sizes, shapes, and materials. In addition, the beads may include one or more "agitator" beads, i.e., a bead with an irregular shape, intended primarily to agitate the other beads, rather than primarily to directly disperse powder.

The chamber 30 preferably has a characteristic dimension (i.e., the diameter for a round chamber; the major axis for an elliptical chamber, etc.) which is from 4 to 20 times greater than the characteristic dimension of the largest bead 40 within the chamber. This allows for sufficient movement of the beads within the chamber, to effectively deagglomerate the drug powder. The beads 40 may be provided with, or manufactured of, a material able to attain a static electrical charge, which may be the same or different to the material of the chamber. The polarity of the charge is selected so that the drug particles are repelled by the beads, to help prevent the particles from sticking to the bead surfaces. The material forming the chamber itself may be similarly charged. The material of the beads and the chamber may be chosen to produce a triboelectric charge upon motion of the beads and air within the chamber. The charge produced may be used to enhance repulsion of the drug particles.

Depending on the specific drug formulation, the bead surfaces may be rough or smooth. Similarly, the beads 40 may be hollow, or solid, or they may be eccentrically shaped, or eccentrically weighted, to achieve desired bead movement and interaction within the chamber 30.

Referring still to FIGS. 1–3, in use, a dose container 48 is placed on the dose platform 46. The dose container 48 is opened releasing a dose of the powdered drug formulation into the inlet 26. The patient inhales on the mouthpiece 22. As this occurs, the optional flow control device 28, if used, opens and air is drawn into the chamber 30 through the inlet opening 41'. The dose of powder deposited in the inlet 26 is drawn into the chamber 30 along with the air flowing into the chamber 30. The inflowing air enters tangentially and moves around within the chamber 30. The air movement drives the beads 40 around in the chamber 30. Due to centrifugal force, the beads 40 will move primarily, but not exclusively, along the race 34, rubbing and colliding with the surface of the race 34, as well as with each other, and with the upper and lower surfaces 31 and 33 of the chamber 30. Although the inlet opening 41 extends through the race 34, the diameter of the inlet opening 41 is small enough, in relation to the size of the beads 40, to avoid extensive disruption of the bead trajectories as they pass over the tangential entry point of the inlet opening. Alternatively, the inlet opening 41 can join into the chamber 30 through a plurality of smaller openings, as shown in FIG. 1A.

As the beads 40 move rapidly about within the chamber 30, the contact, collisions, shear effects, etc. disperse the powder formulation. With formulations having excipient or other carrier particles, the moving beads, together with the shear and other effects described above, tend to cause the smaller active drug particles to separate from themselves and/or the larger carrier particles. Referring to FIG. 3, as virtually all interior surfaces of the chamber 30 can be contacted by the moving beads 40 and the larger carrier or other particles (if any), very little fine powder is held up within the chamber. This means that, most, if not virtually all of the fine powder, initially contained in the dose container 48, is available to be inhaled out of the mouthpiece 22 and inhaled by the patient.

The beads preferably move with a circulation period determined by the interaction of the air jet with the beads in the chamber. The circulation period is preferably less than about 30 milliseconds. In terms of rpm, the bead velocity is preferably about 200–10,000 rpm in the chamber, and preferably from 500–5000 rpm with powder in the chamber. Via the patient's inspiration, the patient inhales (through the nose or mouth) the dispersed powder and air.

As shown in FIGS. 2 and 3, obstructions 54 may be located within the chamber 30, near the race 34, to divert the beads 40 momentarily away from the race 34 (in any direction), to create chaotic bead movement, to better facilitate bead contact with all of the chamber surfaces. Chaotic bead movement means movement of the beads in a less than an entirely uniform manner around the race. The obstructions 54 may be formed as ridges on the surfaces 31 or 33, or as projections on the surfaces 31, 33, or on the race 34. Chaotic bead movement may also be achieved by adjusting other flow parameters to achieve less uniform flow. Specifically, the air inlets 27 can be sized and shaped to cause a transition of bead movement patterns, i.e., with the beads movement changing from more uniform to less uniform, and eventually to chaotic as flow rate increases. This in turn will cause a change in the fine and/or larger particle dispersion efficiencies, with changing flow rates.

Referring momentarily to FIGS. 10A–13B, the chamber 30 may be circular, and disk-shaped (i.e., a cylinder having a diameter greater than its height) as shown in FIG. 2, or it may be elliptical or oval, as shown in FIGS. 10A and 10B; toroidal, as shown in FIGS. 11A and 11B (with a solid or filled in central area 111); or in a bi-concave disk shape, that is, round or circular, but curving inwardly towards the center on the top and bottom surfaces (in the shape of a human red blood cell), as shown in FIGS. 12A and 12B; or round with an extended sidewall transition 132, as shown in FIGS. 13A and 13B. Of course, other chamber shapes may also be used, with or without the sidewall transition surfaces connecting the curved race to the flatter surfaces 31 and 33, as shown in FIGS. 13A and 13B.

While FIGS. 1–3 show an inhaler 20 intended for use with discreet individual dose containers 48, FIGS. 4–7 and 40 show inhalers 60 and 288 for use with multiple dose containers. Referring to FIG. 4, in the multiple dose container inhaler 60, a dose ring or disk 64 is attached on top of an inhaler housing 62. The dose ring 64 has a plurality of dose containers 66, such as dose wells on a cassette ring, as described, for example, in U.S. Pat. Nos. 5,577,497 and 6,006,747, incorporated herein by reference, or blisters as described, for example, in U.S. Pat. No. 5,622,166, both incorporated herein by reference. Alternatively the inhaler 60 may have bulk powder storage and a dose metering device, as is well known in inhaler-technology. FIG. 40 shows a similar design using a blister disk 290, as described in U.S. Pat. Nos. 5,622,166 and 5,921,237, both incorporated herein by reference.

Referring to FIGS. 4–7, the inhaler 60 has an inlet 72 extending into the housing 62 and connecting into a dispersion chamber 74. An outlet 76 at the front end of the dispersion chamber 74 connects into a mouthpiece 70. One or more beads 40 are contained within the dispersion chamber 74, as described above with respect to the inhaler 20 shown in FIGS. 1–3. In use, a dose is released from a dose container 66, passes through a chute or opening 79 and into the chamber 74. The patient inhales on the mouthpiece 70, causing the beads 40, drug dose, and air to move about, producing a powder aerosol for inhalation, as described above.

FIGS. 8A and 8B show an alternative dispersion chamber embodiment which may be used with the inhaler 20 shown in FIGS. 1–3, or with the inhaler 60 shown in FIGS. 4–7. As shown in FIGS. 8A and 8B, an inlet 84 joins tangentially into the chamber 82. The chamber 82 is similar to the chamber 74 shown in FIGS. 4–7, but includes a first or front outlet 86, as well as top outlets 88, connecting to the opening passing through to the mouthpiece 70.

As shown in FIG. 8D, outlets 89 through the top plate 25 may be elongated openings or slits extending radially outwardly. FIG. 8E shows a single horizontal slit opening 37 passing through the circumferential wall 29, connecting the inlet opening 41 into the chamber 30 in contrast to the multiple openings shown in FIG. 1A. A vertical slit opening 43 may also be used, as shown in FIG. 8F.

In the embodiments shown in FIGS. 1–8B, the dispersion chamber is oriented horizontally. The bottom surface 33 is directly underneath the top surface 31, with respect to gravity and the central axis of the chamber, designated A, in FIG. 3, is vertical. In contrast, as shown in FIG. 9, in an alternative embodiment, the dispersion chamber 92 is oriented vertically, and has a central axis B which is horizontal. Outlets 96 are arrayed along the front surface of the chamber 92, with an inlet 94 at the bottom of the chamber 92.

The flow control device 28 may be provided to limit flow, so as to moderate the bead motion within the chamber, as driven by the patient's inspiratory force. The flow control device 28 may be one or more separate components, e.g., it may have a flow control limiter component and a separate flow trigger.

Figure 14:
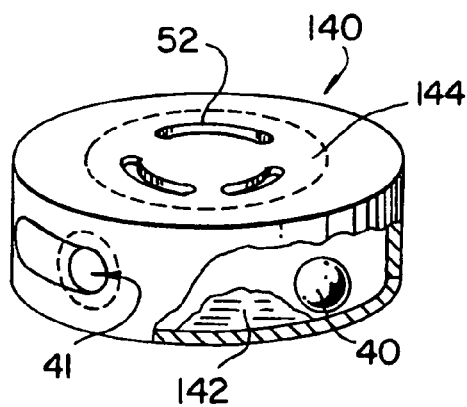
FIG. 14 is a perspective view, in part section, of a separate disposable dose chamber.

The powder dose may be provided directly in the dispersion chamber 30, 74, 82 or 92, during manufacture of the inhaler, as an alternative to the single dose container 48. Referring to FIG. 14, the dispersion chamber may also be made as a separate component 140 containing beads and a powder dose 142, and insertable into the inhaler, to provide a single dose, for use as a disposable and a replaceable unit. The inlet 41 and outlet 52 are covered with a tape cover 144 or other seal or cover, which is removed before use. Providing the dispersion chamber as a separate removable and/or replaceable component (optionally attached to the mouthpiece) allows the patient to discard or blow out an unintended dose (e.g., a stale dose, a double dose, etc.). It also allows the dispersion chamber to be removed for cleaning the inhaler.

An outlet hole 150 normal to the radial wall of the chamber, as shown in FIG. 2, may be provided, to control the residence time of larger particles within the chamber.

Figure 7:
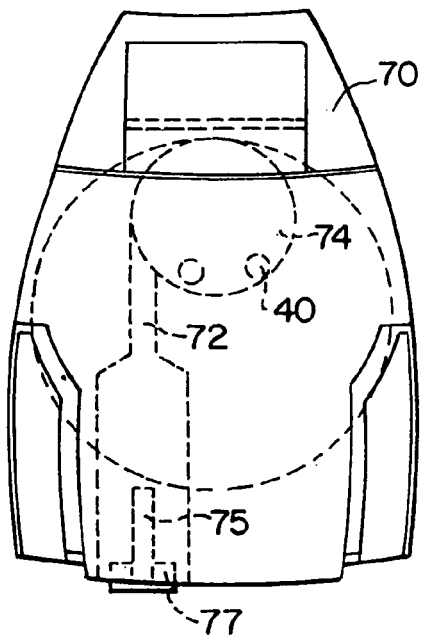
FIG. 7 is a bottom view thereof.
Figure 5:
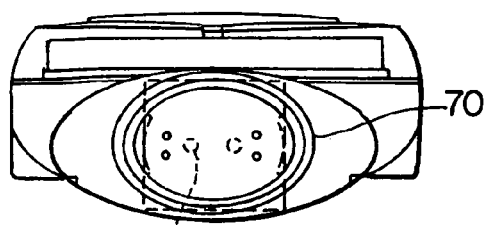
FIG. 5 is a front view thereof.
Figure 6:
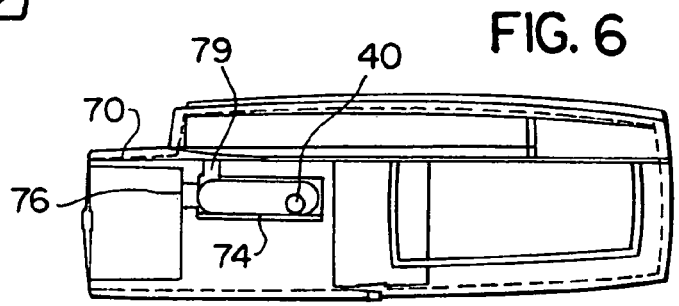
FIG. 6 is a side view thereof, in part section.
Figure 10A:
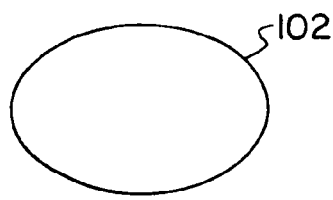
FIG. 10A is a top view of an alternate dispersion chamber, having an oval shape.
Figure 12A:
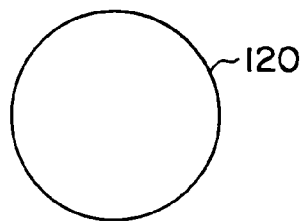
FIG. 12A is a top view of an alternative dispersion chamber design having a concave annular shape.
Figure 10B:
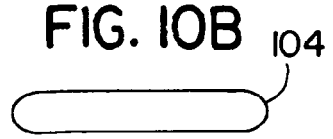
FIG. 10B is a side view thereof.
Figure 12B:
FIG. 12B is a section view thereof.
Figure 11A:
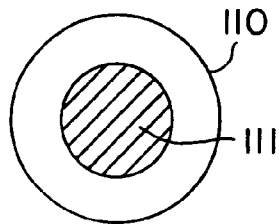
FIG. 11A is top view of an alternate dispersion chamber design, having a toroidal shape.
Figure 13A:
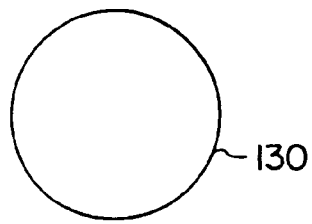
FIG. 13A is a top view of an alternative dispersion chamber design having a sidewall transition.
Figure 11B:
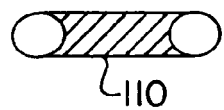
FIG. 11B is a section view thereof.
Figure 13B:
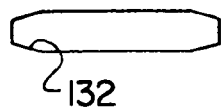
FIG. 13B is a side view thereof.

The inhaler may be provided with a feedback device such as a vibrating element, or a whistle or tone generator 75, as shown in FIG. 7. A reed or other vibrating member produces a sound or tactile vibration which turns on or changes in pitch based on the patient's inspiratory flow rate. In this way, the patient can be trained to inhale at the proper flow rate, via the feedback provided by the tactile vibration or sound generated by the patient's inspiration. The feedback device 75 is preferable located at the upstream end of the inhaler (upstream of the powder path), as shown in FIG. 7. If the feedback device is a sound generator, a button or switch 77 is also preferably provided to allow the patient to switch the sound generator off, so that the inhaler may be used discretely.

In addition to a sound or tactile vibration, the flow indicator 75 may be a button that changes position indicating the user has generated at least a minimally desired flow rate through the inhaler. The pressure drop of air flowing through the inhaler, preferably through the sheath airflow path, would provide the force to drive the flow indicator.

For certain applications, the chamber may be manufactured of a transparent material. Upon use, the chamber changes from clear to cloudy or opaque with a predetermined amount of deposited particles, providing a visual indication to the patient that the replaceable chamber has been used.

Preferential dispersion and retention of particles may be enhanced through triboelectric charging by selection of appropriate materials.

Figure 15A:
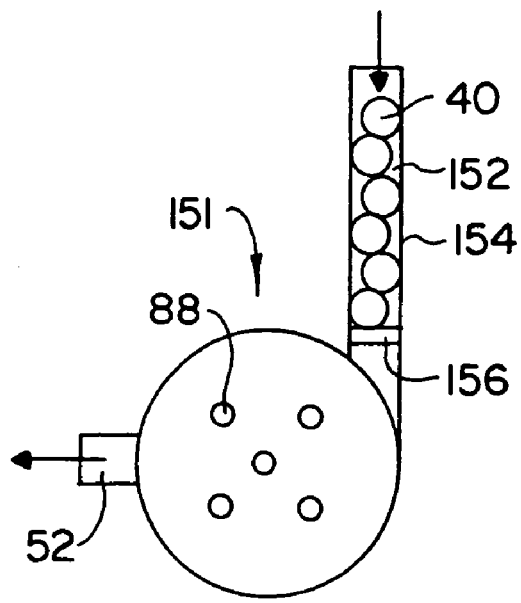
FIG. 15A is a schematically illustrated plan view of an inhaler embodiment having beads stored in a compartment separate from the dispersion chamber, before use.
Figure 15B:
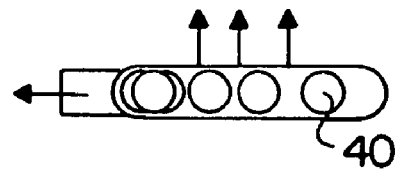
FIG. 15B is a side view thereof.

FIGS. 15A and 15B show an inhaler embodiment 151 having beads 40 stored in a storage compartment 152 within an inlet tube 154. A retainer/flow trigger 156 holds the beads in the compartment. Upon inhalation by the patient, the retainer/flow trigger opens, releasing the beads into the chamber. The beads disperse powder in the chamber, as described above. The sudden release of the beads provides a boost to bead movement and dispersion. The flow trigger 156 or beads 40 can also act as a backflow preventer, to prevent the patient from exhaling into the inhaler. In addition, the presence of the released beads in the chamber and any non-dispersed particles, following delivery of the dose, provides a tactile, visual and sound indication that the inhaler has been used and is spent. The powder may be provided with the beads 40 in the storage compartment, or it may be prefilled into the chamber, or be delivered into the chamber from a cassette, a blister disk or a bulk powder dispenser.

Figure 16A:
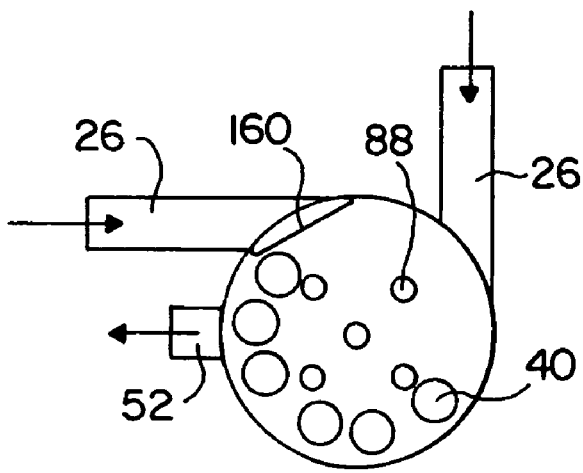
FIG. 16A is a schematically illustrated plan view of an inhaler embodiment similar to the design shown in FIG. 8A, but with two inlets.
Figure 16B:
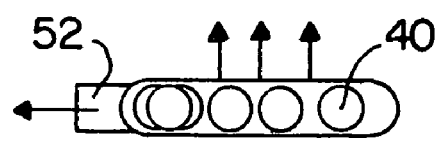
FIG. 16B is a side view thereof.

FIGS. 16A and 16B show a design similar to FIGS. 8A and 8B, but with two radially spaced apart inlets 26. One of the inlets may include a flow trigger 160 which opens only upon reaching a specified threshold of pressure drop or flow rate. The opening of the flow trigger 160 can be used to change the pattern of bead movement.

A surprising result of the inhalers above having beads is that the presence of the moving beads substantially reduces the flow resistance of the inhalers, for both uniform and chaotic bead movement. At 10 liters per minute (lpm) of flow, the reduction in flow resistance is about 15–33%, using from 1–11 beads, compared to flow resistance with no beads, and the reduction is about 23–33% using 2–11 beads. For the embodiment shown in FIG. 16A having 2 inlets, at 10 lpm, using 6 beads, flow resistance was reduced by 40%, when compared to the same inhaler with no beads. This reduction increased to 44% at 15 lpm. These reductions in flow resistance are counterintuitive because the beads reduce the flow cross sections within the inhaler. Thus, one would expect the presence of the beads to increase, rather than decrease, the flow resistance.

This reduction in flow resistance provides the advantage of allowing more air to flow through the inhalers at any given pressure drop (inspiration or suction force of the patient). This increase in flow increases powder dispersion, without any increase in patient effort.

Figure 18:
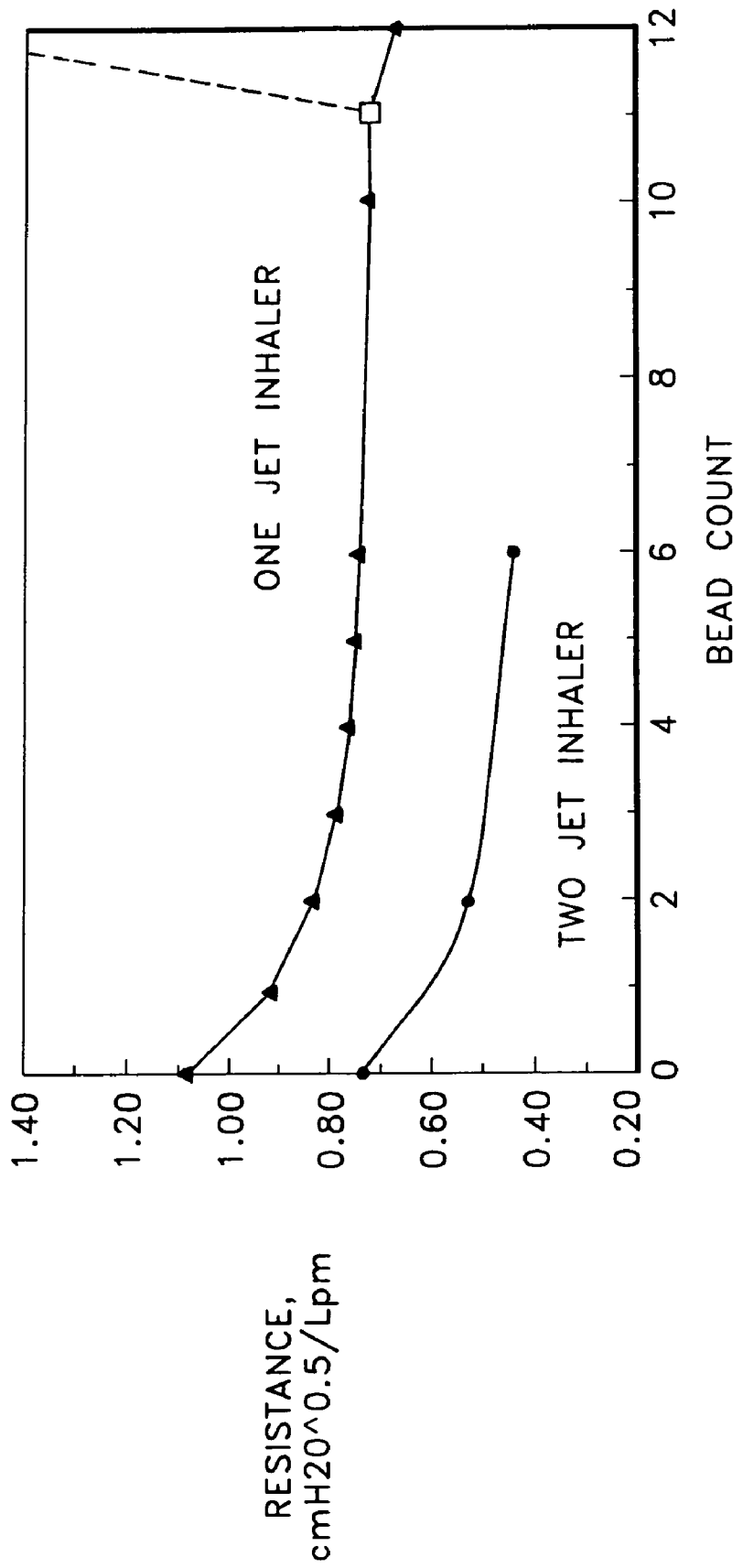
FIG. 18 is a graph of the data shown in FIG. 17.

FIG. 17 shows data on the reduction of flow resistance via use of beads, for one and two jet (inlet) inhalers, as shown in FIGS. 1 and 16A. FIG. 18 shows the data in graphical form.

FIG. 19 shows in-vitro aerosol performance data for the inhalers with one and two inlets or jets, as shown in FIGS. 1 and 16A. Using dry powder formulations of budesonide and lactose resulted in budesonide respirable fractions between 34–48%, as shown in FIG. 19. Each of the 3 inhalers were tested with a total of 4 separate aerosol samples. The average and standard deviation of respirable fraction for each model was 36.3±1.7% (Model 1), 42.9±1.2% (Model 2), and 44.7±2.1% (Model 3). Thus, the inhaler performance, in terms of respirable fraction, airflow resistance, powder holdup, and reproducibility of dose, is very good, in comparison to existing inhalers.

The inlet in the Figures described above is straight, tangent, and non-angled relative to the bead chamber, with a rounded-rectangular inlet cross section. The outer wall of the inlet is tangent to the bead race. Alternative inlet designs may be used to enhance performance. As shown in FIG. 20, an inlet tube or opening 200 may be angled relative to the plane of the bead chamber 206. As shown in FIG. 21, a scoop inlet 202 has an inner edge or will that is tangent to the outer diameter or surface of the bead race. As shown in FIG. 22, a chord inlet 210 enters into the bead chamber non-tangentially along a chord 212. The inlets 200, 202 or 210 may be non-angled, i.e., extending in the plane of the bead chamber, or they may be angled, as shown in FIG. 20.

With the scoop inlet 202 shown in FIG. 21, the outside wall of the inlet is positioned to the outside of a tangent to the bead race: With a scoop inlet having maximum offset, the inside wall of the inlet is tangent to the outside of the bead race. The airflow from this inlet is directed into the bead chamber via a scoop connection over a longer arc length, in comparison to the tangent inlet 26 shown in FIGS. 1, 2 and 23. This entry of air over a longer arc length preserves the driving force to circulate the beads and powder, increasing the exposure of the fluidized powder to the shear stresses created by air flowing rapidly into the chamber from the inlet 202. Consequently, powder dispersion may be more efficient. This design also reduces the accumulation of particles often seen on the circumference of the bead chamber and immediately before the inlet.

The chord inlet 210 in FIG. 22 extends along a chord 212, rather than a tangent, to provide different flow and circulation patterns within the bead chamber. Testing shows that the beads pass directly through the inlet airflow, maintaining normal bead motion and contact with the bead race, so that powder is dispersed efficiently. The transient accumulation of fluidized particle concentrations at the inside edge of the inlet is reduced and additional airflow shear is present in the area of the bead chamber outside the chord formed by the inlet, which may improve particle dispersion. There also appears to be more and larger scale turbulence within the bead chamber. This may subject particles to greater and more varying shear stresses, which can also enhance dispersion, even while the beads continue to contact all surfaces around the race. This inhaler design has been shown to aerosolize powder efficiently at least as well as tangential inlet design, (similar emitted and respirable doses, 96% versus 92% dose delivery within 0.5 seconds at 30 lpm, respectively).

Figure 4:
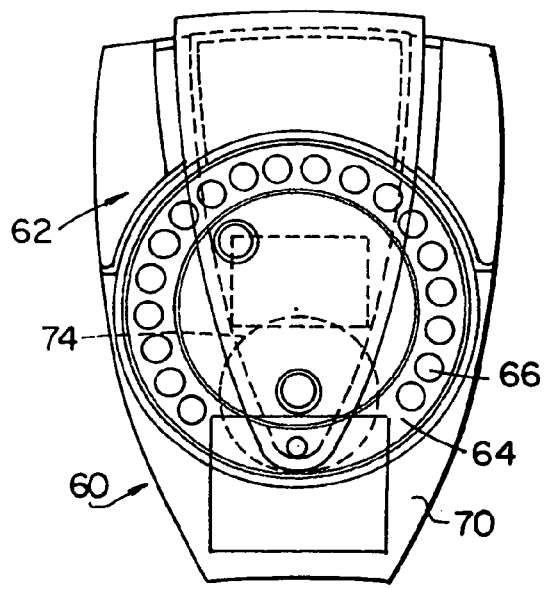
FIG. 4 is a top view of a second embodiment.
Figure 40:
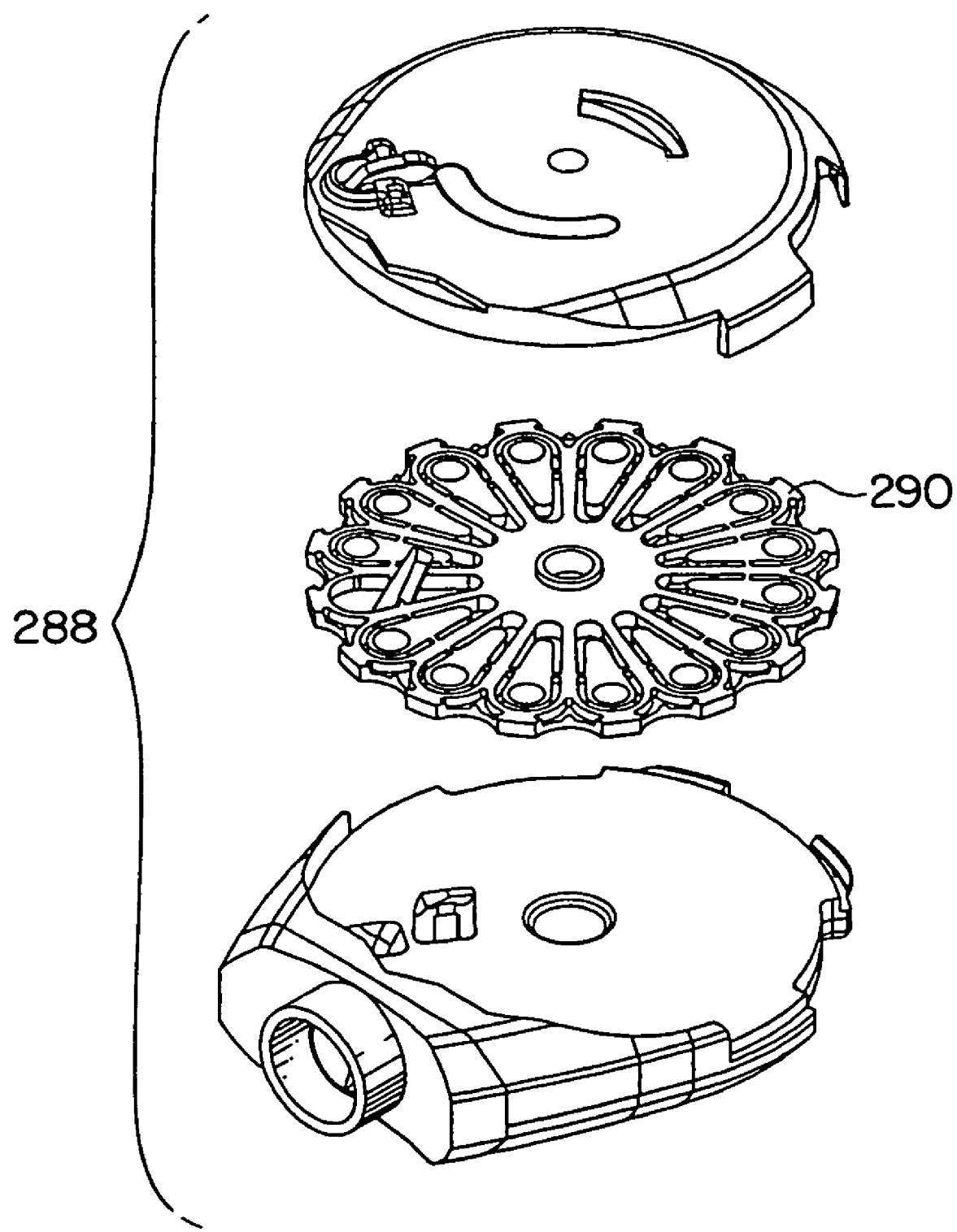
FIG. 40 is an exploded perspective view of an inhaler body or housing, a blister disk, and a lid, with the inhaler body including a dispersion engine as shown in one or more of FIGS. 20–39.

The inlets 26, 200, 210 and 202, or combinations of them, may also be curved to efficiently connect the blister disk 290, shown in FIG. 40, or the dose ring 64 shown in FIG. 4 (or other powder storage component, e.g., a bulk container, blister strip or tape, a mesh, string, capsule, etc.), with the dispersion chamber. The inlets may also have alternate cross sections, smooth or rough walls, and may also include flow directors, to control the flow resistance and flow pattern entering the dispersion chamber. Other shapes and features may be added such as guides at the inlet/bead chamber interface, to retain beads within the chamber, flow directors to control airflow patterns within the bead chamber, or combinations of them and help control airflow patterns. A guide is a bridge or section extending across the inlet opening, as shown in FIG. 1A. A flow director is a structure in front of, or part of, a guide, used to direct flow, such as a vane or louver.

Sheath air is ambient airflow used reduce particle deposition in the mouthpiece. Sheath air is air drawn into the mouthpiece without passing through the powder flow path of the inhaler. While use of sheath air reduces particle hold up in the mouthpiece, it also reduces the amount of airflow available to move powder through the inhaler for inhalation. Consequently, the flow split between the sheath air path and the powder air path should be appropriately balanced. Typically, the flow split will range from about 30–95%, or more preferably 40–70% of the total airflow (as inspired by the patient) moving through the powder flow path, with the balance moving through the sheath air path. Both flows combine within the inhaler mouthpiece to for the total flow through the inhaler, as generated by the patient's inspiration.

As shown in FIG. 24, sheath air inlets 220 preferably extend radially inwardly to a ring 222 in the mouthpiece tube 224, to provide an annular flow of sheath air 226 surrounding the flow of powder laden air 228 in the mouthpiece. As shown in FIG. 25, another sheath air mouthpiece 30 surrounds a dispersion chamber 240 having an elongated exit tube 242. This provides an outer approximately annular region 245 of axial sheath airflow to limit physical contact and deposition of dispersed particles to the walls of the mouthpiece. The sheath airflow increases the efficiency of powder transfer from the inlet to the outlet of the mouthpiece.

Dispersed particles released into a mouthpiece have trajectories not directed solely toward the outlet of the mouthpiece. Further, these particles are often emitted from an area smaller than the cross-section of the mouthpiece. This leads to airflow turbulence and back eddies that can lead to particle deposition inside the mouthpiece. Consequently, it is important for the mouthpiece to efficiently transfer particles from the point of dispersion to the mouthpiece outlet (which is placed in the patient's mouth).

The tube 242 may have a length ranging from 0.5 to 13 mm (0.02 to 0.5 inches) if used with a sheath air mouthpiece. Alternatively, if no sheath air is used, the outlet tube may be even longer to serve as the mouthpiece, or it can made shorter and lead into a larger mouthpiece. The outlet tube 242 may advantageously provide a region of high shear, to help dispersion of particles. It is also a region or path of high velocity, to better transport the aerosol or drug particle/air mixture efficiently into the mouthpiece. The elongated outlet tube 242 may also better direct sheath air into the mouthpiece, along its outside surfaces, to further reduce particle deposition. The outlet tube 242 preferably approximates a right circular cylinder with an angle of expansion between −15 and +15 degrees, to control velocity profiles and limit particle deposition.

The sheath air mouthpiece shown in FIG. 25 provides a continuous or near-continuous approximately annular sheath of airflow directed axially through and out of the mouthpiece. The sheath air is not drawn from the dispersion chamber or other region where particles are generated or dispersed. This is intended to provide sheath air, which is largely free of the pharmaceutical particles being dispersed.

The velocity of the sheath air is preferably approximately matched to, and not excessively greater than, the velocity of the air flowing into the mouthpiece from the dispersion chamber outlet.

As shown in FIG. 25, the non-cylindrical sheath-air mouthpiece 230 has an expanding cone 232. In this mouthpiece 230, the sheath air flows forward (towards the patient's mouth), and also expands along the cone 232. The cone angle is made gradual to reduce the effects of flow separation and resulting pressure drop and particle deposition.

If, due to flow characteristics, the dry powder pharmaceutical particles flow out of the dispersion chamber towards the walls of the mouthpiece, the design may be modified to provide a thicker layer of sheath airflow between the particles and the wall. This may be accomplished by asymmetrically varying the thickness of the thickness of the sheath air annulus 245 to create a thicker sheath airflow in regions where particles would otherwise contact and settle out in the mouthpiece. The thicker layer of sheath air is provided to absorb and redirect the particles flowing in trajectories towards the interior mouthpiece walls, and to limit contact between the particles and the walls of the mouthpiece. The sheath air annulus need not be ring shaped, like a true geometric annulus. It may be flattened, with thicker side lobes connected by thinner web sections. This can be done preferably by having an exit tube with a round outside surface surrounded by inner walls of the mouthpiece tube shaped in an ellipse, oval, or other flattened or elongated curved shape.

The outlet 234 into the mouthpiece need not be centered in the mouthpiece inlet 236. It may be off center with the optionally thickened sheath air layer introduced between the dispersion outlet 234 and the cylindrical or conical wall 232 of the mouthpiece.

Tests on mouthpieces with sheath air show improved performance relative to the conventional inhaler design. Hold-up within the mouthpiece was reduced to about 30–50% of the holdup in an equivalent inhaler without sheath air. Computational fluid dynamics models indicate that particle deposition within the mouthpiece may be reduced by 70% or more using sheath air. Hold up is the amount of medicament remaining in the mouthpiece after use.

The advantages of providing sheath air include: (1) increased particle delivery efficiency, (2) reduced priming effect, (3) reduced cleaning requirements, (4) increased dosing precision, (5) reduced manufacturing costs (e.g., less drug required), and (6) greater aerosolization efficiency in the sheath air shear field. The priming effect is the tendency for initial doses to be reduced due to deposition on the mouthpiece surfaces.

While the description of sheath air above is made primarily with reference to the specific inhalers shown in the drawings, the features and principles described apply as well to any inhaler having a mouthpiece, regardless of the dispersion mechanism, powder or other drug media storage and release technique, and powder or drug media flow or movement designs used.

Figure 29:
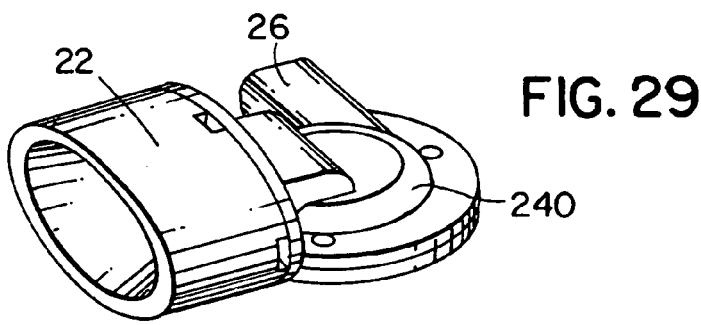
FIG. 29 is a perspective view of an inhaler having a horizontally oriented dispersion chamber.
Figure 31:
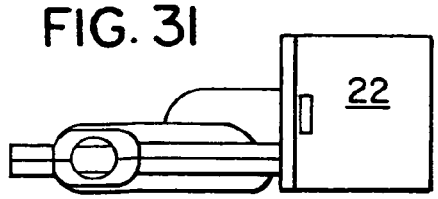
FIG. 31 is a left side view thereof.
Figure 32:
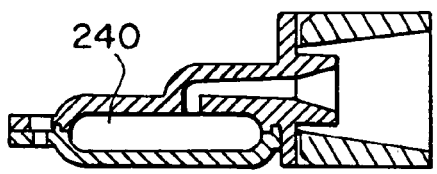
FIG. 32 is section view thereof.
Figure 30:
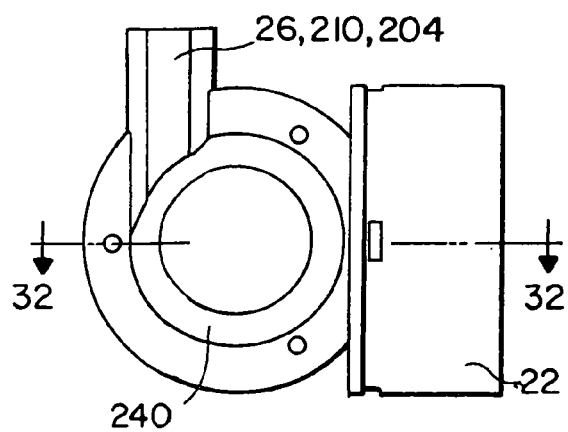
FIG. 30 is top view thereof.

To reduce the size of the inhaler, reasons, the bead or dispersion chamber of the inhaler is preferably horizontal in use as shown in FIGS. 1–7, 29–35 and 40. Referring for example to FIG. 29, the dispersion or bead chamber such as 30, 82, 240, etc. is horizontal, i.e., the top and bottom walls of the bead chamber are in a horizontal plane (with respect to gravity), when the inhaler is in use. The mouthpiece such as 22, 224, 232, etc., or more specifically the flow of the air/powder aerosol out of the mouthpiece, is also horizontal. In this design, the chamber is then necessarily connected to the mouthpiece with a right angle connection, as shown in FIG. 29. This allows the height of the inhaler to be reduced, providing a more compact design. The particles flowing out of the bead chamber are diverted by about 90° into an outlet duct. To limit particle deposition, the outlet duct preferably expands at an angle of less than 15° as it approaches the mouthpiece. FIGS. 8A–F, 15A and B, and 16A and B and 20–39 show dispersion engines, some including a mouthpiece, for use in an inhaler, which typically will also include a powder storage system or component, such as a blister disk, dose ring, bulk reservoir, capsule(s), etc.

The bead chamber must be designed to contain the bead(s) and to prevent the bead(s) from escaping from the chamber and moving into the mouthpiece. Various bead isolation or containment features may be used for this purpose, thus allowing more options in the design and selection of the outlet holes, e.g., the outlet holes may be larger than the bead diameter or smallest characteristic bead dimension. The bead isolation and/or containment features may be combined as a backup to prevent release of beads from the inhaler.

Figure 33:
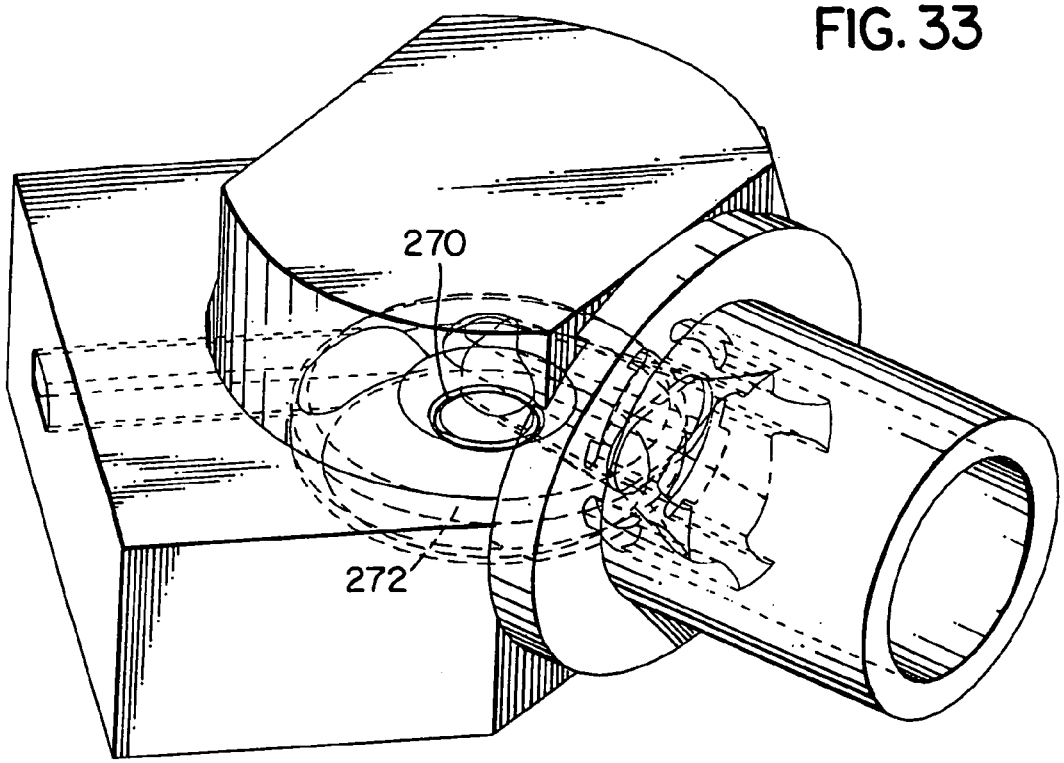
FIG. 33 is perspective view of an inhaler having a bead retention feature.
Figure 34:
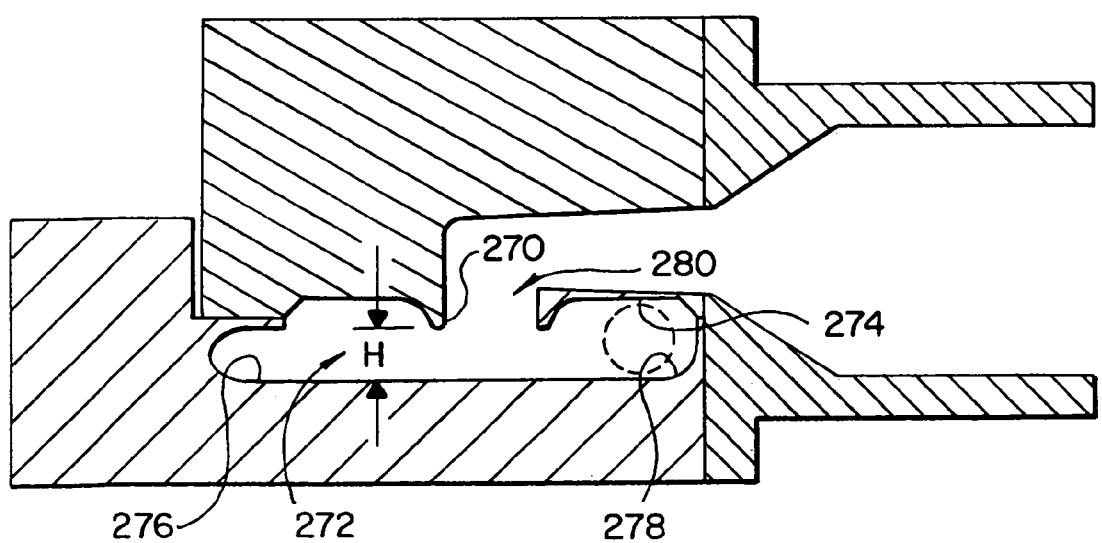
FIG. 34 is a section view thereof.

As shown in FIGS. 25, 33 and 34, a chamber ring 270 extends inwardly into the bead chamber 272 from the top surface or wall 274 of the chamber, towards the bottom surface 276 of the chamber. The ring 270 extends down so that the opening H is small enough to prevent any bead from moving out of the race 278 and into the outlet 280.

Figure 35:
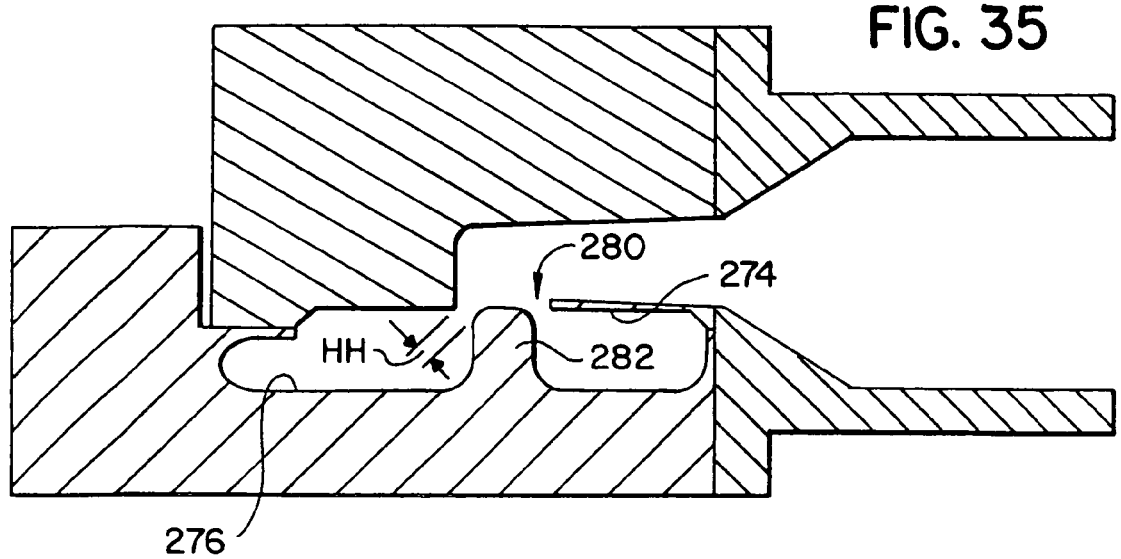
FIG. 35 is a section view of an alternative bead retention feature.
Figure 36:
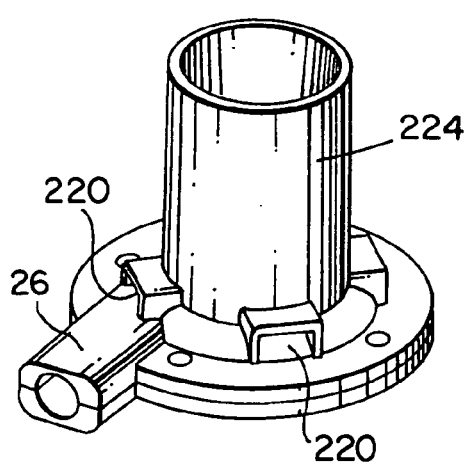
FIG. 36 is a perspective view of the inhaler, or the dispersion chamber and mouthpiece shown in FIG. 24.
Figure 37:
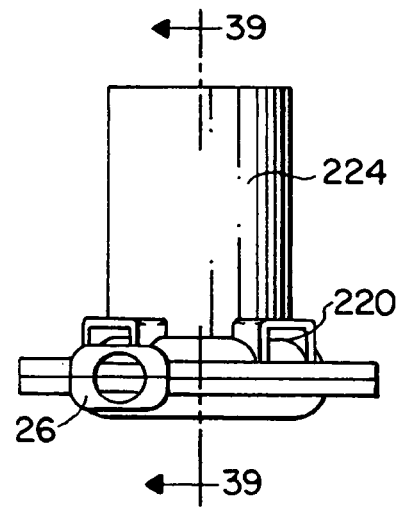
FIG. 37 is a left side view thereof.
Figure 38:
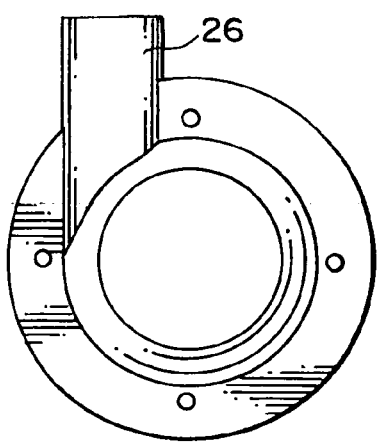
FIG. 38 is a top view thereof.
Figure 39:
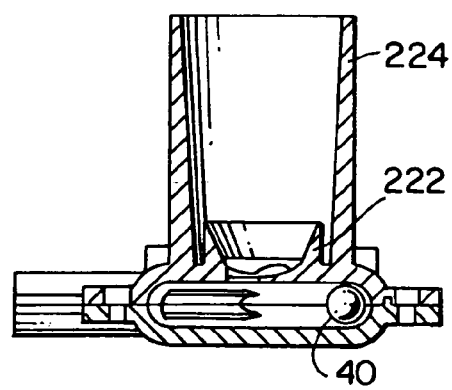
FIG. 39 is a section view thereof.

As shown in FIG. 35, in an alternative design, the beads are contained by a central protrusion or land area 282 extending up from the bottom surface of the bead chamber. The land area limits clearances around the outlet hole 280 to less than the diameter or smallest dimension of the bead(s).

One or more outlet openings connect the bead or dispersion chamber with the mouthpiece. The shape of the opening (s) may be circular or non circular. The outlet opening(s) may be centered with or on the chamber, offset from the center of the chamber, and/or in an asymmetrical pattern. FIG. 2 shows a vertical outlet 52 extending upwardly parallel to the chamber or race axis, and a horizontal outlet 150 extending horizontally and forwardly towards the mouthpiece, and perpendicular to the chamber or race axis.

Figure 26:
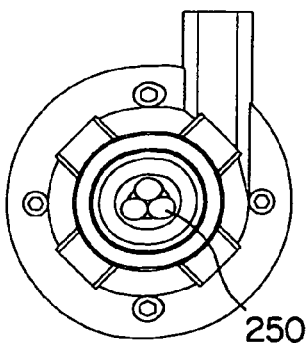
FIG. 26 is a front view of a dispersion chamber having a three hole outlet.
Figure 27:
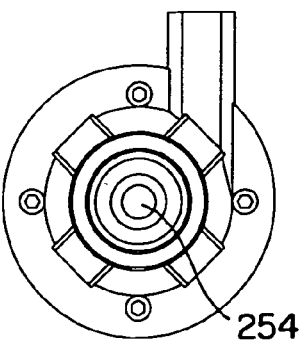
FIG. 27 is a front view of a dispersion chamber having a single center hole outlet.
Figure 28:
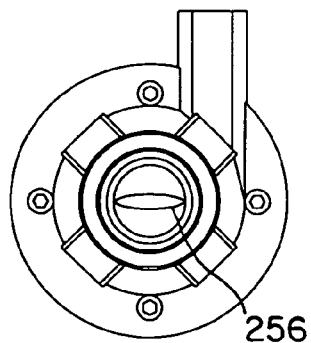
FIG. 28 is a front view of a dispersion chamber having a slotted outlet hole.

Non circular shapes such as triangles or slots may be used. Narrow but wide slotted outlets provide less opportunity for bead jamming and may allow for faster removal of larger particles. FIG. 26 shows a dispersion chamber outlet having three outlet holes 250 adjacent to or contacting each other, and centered in the dispersion chamber 30, 206, 240, etc. FIG. 27 shows a single outlet hole 254 centered in the chamber, and FIG. 28 shows a slotted or elliptical opening 256, also centered in the chamber. These and other types of openings may also be made off-center, or repeated to provide multiple openings. If the openings are small or narrow enough across one dimension (such as a narrow slot), then the opening(s) can used to contain the bead(s) within the chamber, and the bead retention or containment features shown in FIG. 34 or 35 are not needed.

In the bead inhalers described above, the air/powder flow path (plus the sheath airflow path, if used) preferably has a flow resistance range of 0.1–0.25 or more preferably $\sqrt{0.12 \text{ to } 0.22 \text{cmH2O}}$ lpm, at standard conditions. The flow rate for these inhalers ranges from 10–70 and more preferably 15–45 lpm.

The various design parameters may be changed or balanced in ways readily obvious to skilled designers.

The inhalers and bead chambers described above are intended for use with one or more beads in the chamber. However, they may also be used without any beads at all. Without any beads, flow resistance through the chambers will generally be higher, as the pressure drop reduction created by the use of beads is not achieved. In addition, the dispersion performance without beads may also be degraded. Still, for some applications, use of any of the chambers described above, without beads, may be preferred.

Thus, a novel inhaler and methods have been shown and described. The inhaler provides various advantages. It can be manufactured at low cost, provide quiet operation to enhance patient discretion, and reduce hold up of powder within the inhaler, as a result of the self-cleaning/scouring action of the beads. The present inhaler also has reduced size and weight, yet has a high efficiency in delivering a dose of dry powder.

Various changes and modifications may of course be made without departing from the spirit and scope of the invention. The invention, therefore, should not be limited, except by the following claims and their equivalents.

What is claimed is:

1. An inhaler comprising:
   a dispersion chamber having an open central interior;
   a bead race in the dispersion chamber;
   one or more beads in the dispersion chamber;
   an inlet connecting into the dispersion chamber;
   an outlet connecting into the dispersion chamber and spaced apart from the inlet; and
   a chamber ring extending partially into the bead chamber, for preventing any bead from moving out of the dispersion chamber and into the outlet.

2. The inhaler of claim 1 wherein the dispersion chamber includes an inner wall forming a bead race, and wherein the bead moves around the bead race upon inhalation by the patient.

3. The inhaler of claim 2 wherein the bead race has a radius of curvature greater than a radius of curvature of the bead.

4. The inhaler of claim 2 wherein the dispersion chamber has a flat bottom surface and a flat top surface adjoining the bead race.

5. The inhaler of claim 1 wherein the bead moves around chaotically in the dispersion chamber when a patient inhales on the outlet.

6. The inhaler of claim 1 further comprising a dose platform adjacent to the inlet, for holding a dose of a dry powder pharmaceutical.

7. The inhaler of claim 6 wherein the bead has or acquires a static electrical charge, and particles of the dry powder also have or acquire a static electrical charge of the same polarity, so that the bead and the particles of dry powder repel each other.

8. The inhaler of claim 1 further comprising an obstruction in the dispersion chamber to cause the bead to move chaotically.

9. The inhaler of claim 1 wherein the dispersion chamber comprises a separate component, installable into, and removable from the inhaler.

10. The inhaler of claim 1 wherein a plurality of beads are located in the dispersion chamber, and wherein at least one of the beads includes a discontinuity.

11. The inhaler of claim 10 wherein the bead having the discontinuity is polygonal shaped, and the discontinuity comprises a corner.

12. The inhaler of claim 10 wherein the bead having the discontinuity comprises a sphere with a flat surface.

13. The inhaler of claim 1 further comprising means for providing feedback to the patient based on an airflow rate in the dispersion chamber.

14. The inhaler of claim 1 wherein from 2 to 10 round beads are provided in the dispersion chamber.

15. The inhaler of claim 14 wherein the beads move around the dispersion chamber at 4000–10,000 rpm.

16. The inhaler of claim 1 wherein the dispersion chamber has a characteristic dimension that is from 4 to 20 times greater than a characteristic dimension of the bead.

17. The inhaler of claim 1 wherein the dispersion chamber has a flat bottom surface and a flat top surface adjoining the bead race.

18. The inhaler of claim 1 with a largest bead in the chamber having a characteristic dimension of at least 50 to 90% of an interior height of the dispersion chamber.

19. The inhaler of claim 1 with the open central interior in the same plane as the bead race.

* * * * *